United States Patent [19]

Asano et al.

[11] Patent Number: 5,013,920
[45] Date of Patent: May 7, 1991

[54] INFRARED ANALYZER WITH IMPROVED CALIBRATION

[75] Inventors: Ichiro Asano, Kouka; Kennosuke Kojima, Ohtsu; Aritoshi Yoneda, Otokuni, all of Japan

[73] Assignee: Horiba, Ltd., Kyoto, Japan

[21] Appl. No.: 526,242

[22] Filed: May 18, 1990

[30] Foreign Application Priority Data

May 20, 1989 [JP] Japan .................................. 1-127597

[51] Int. Cl.[5] ...................... G01D 18/00; G01N 21/61
[52] U.S. Cl. ................................ 250/343; 250/252.1;
                                    250/339; 250/345; 250/349
[58] Field of Search ..................... 250/343, 252.1, 339,
                                                250/345, 349

[56] References Cited
U.S. PATENT DOCUMENTS 4,673,812  6/1987  Yoneda ............................ 250/252.1
4,684,805  8/1987  Lee et al. ............................ 250/343
5,255,627  1/1985  Krempl et al. ...................... 250/345

Primary Examiner—Constantine Hannaher
Assistant Examiner—Edward J. Glick
Attorney, Agent, or Firm—Price, Gess & Ubell

[57] ABSTRACT

An improved infrared analyzer is provided wherein an unknown specimen gas can be subjected to a measuring infrared ray and a comparative infrared ray to provide resulting signals. The system can be initially calibrated when a zero gas state is initially achieved in the sample cell, and correction factors are achieved by holding the zero gas instrument signal and an output difference between a zero gas comparison signal and the measuring signal for subsequent processing of the actual measurement of the specimen gas to provide a calibrated output signal representative of the concentration of the unknown gas.

7 Claims, 2 Drawing Sheets

INFRARED ANALYZER WITH IMPROVED CALIBRATION

BACKGROUND OF THE INVENTION

1. Field of the Invention

The present invention relates to an infrared analyzer and, more particularly, to an infrared analyzer having an improved calibration capability.

2. Description of Related Art

Infrared analyzers, used in the prior art, direct infrared rays from a light source through a sample cell into which a sample gas is introduced. The difference between a measured signal that is proportional to the energy of an infrared ray having a characteristic of absorption in a wavelength range of a specific ingredient gas and a comparative signal that is proportional to the energy of an infrared ray having a wavelength that is not absorbed, or at least subject to a negligible absorption, is determined. This difference can be amplified to determine the concentration of the specified ingredient gas from the sample. To ensure the accuracy of this measurement, both a zero calibration and a span calibration must be periodically conducted on the instrumentation at frequent intervals. In the process of providing a zero calibration, the sample cell is evacuated or a "zero" gas state is introduced into the sample cell, and after an indication of a stabilization of the system, measurements are taken to reflect the characteristics of the instrument system per se. Subsequently, a span gas of a known purity is introduced into the sample cell, and again after a stabilization period, a span calibration is then conducted. These measurements can then be utilized to ensure an accurate calibration of the infrared analyzer.

A problem has existed in that an expensive span gas having a high degree of purity must be used at every span regulation in order to verify the gas calibration. Thus, the cost of the calibration can become relatively expensive and time consuming.

Alternative calibration methods, such as a mechanical calibration method, have been suggested in the prior art. In this method, the intensity of the light passing through the cell is physically reduced by means of a metallic plate and a filter to thereby change the quantity of the light incident upon the sensor detector. The characteristics of the metallic plate and the filter are known, and thereby a comparison with the output of the infrared analyzer can determine whether the system is appropriately calibrated. In the mechanical calibration method, numerous problems can occur, such as a misalignment of the metallic plate, and these problems can directly affect the sensitivity of the measurement system in a subtle manner that may not be easily discovered and may be treated as an instrument error. Additionally, in the case where a filter is used to reduce the intensity of the light passing through the sample cell, the filter itself can become physically stained or damaged, and can thereby change the quantity of the light. As can be appreciated, the mechanical calibration method, while less expensive than the use of an expensive span gas, still exhibits numerous disadvantages that plague the prior art.

A Japanese Patent Application Laid-Open No. Showa 61-20840 sought to solve the disadvantages of the above-described gas calibration method and the mechanical calibration method. This patent disclosure teaches a method wherein a zero gas state is measured, an input is then changed to the same extent as the absorption by the gas, and an amplifying factor is changed so that the change in the input signal may amount to an appointed change to conduct the span calibration. This method, however, still requires the span regulation to be conducted after the zero-point regulation, and increases the time period of the calibration.

Accordingly, the prior art is still seeking to optimize the calibration of the accuracy of infrared analyzers in an economical and time efficient manner.

SUMMARY OF THE INVENTION

The present invention seeks to provide an infrared analyzer that is capable of not only conducting a zero point calibration and a scan gas calibration with high accuracy, but further, to conduct these calibrations at not only the same time, but also for a relatively short period of time, without the use of an expensive span gas. Thus, the cycle of using an expensive span gas can be supplemented by the present invention to maintain the accuracy of the instrument with the span gas providing only a periodic verification.

The infrared analyzer of the present invention permits either a gas having no absorption effect at a characteristic absorption wavelength of the specified ingredient gas to be introduced into the sample cell, or an evacuation of the sample cell, to determine both a zero gas measured signal and a zero gas comparative signal. A differential signal is then obtained from these signals and amplified. This differential signal is then subtracted from a second differential signal attained by amplifying the difference between a comparative signal and a measured signal when a sample gas is measured. The difference between the comparative signal and the measured signal can then be divided by the zero gas measured signal to assist in determining the concentration of the specific ingredient gas. By utilizing the above construction, the span calibration does not require the introduction of an expensive span gas into the sample cell. The zero gas measured signal, obtained when a zero gas state is measured, has been memorized, and the resulting calculation is conducted on the basis of this memorized zero gas measured signal. Thus, the span calibration can be simple and inexpensively conducted and, further, the zero calibration and the span calibration can be conducted at the same time in a relatively short period of time.

The object and features of the present invention, which are believed to be novel, are set forth with particularity in the appended claims. The present invention, both as to its organization and manner of operation, together with further objects and advantages thereof, may best be understood by reference to the following description taken in connection with the accompanying drawings.

DESCRIPTION OF THE PREFERRED EMBODIMENTS

The following description is provided to enable any person skilled in the analytical gas measurement field to make and use the invention, and sets forth the best modes contemplated by the inventors of carrying out their invention. Various modifications, however, will remain readily apparent to those skilled in the art, since the generic principles of the present invention have been defined herein specifically to provide a relatively economical, reliable, and highly accurate infrared analyzer that can be calibrated with precision and speed.

Figure 1:
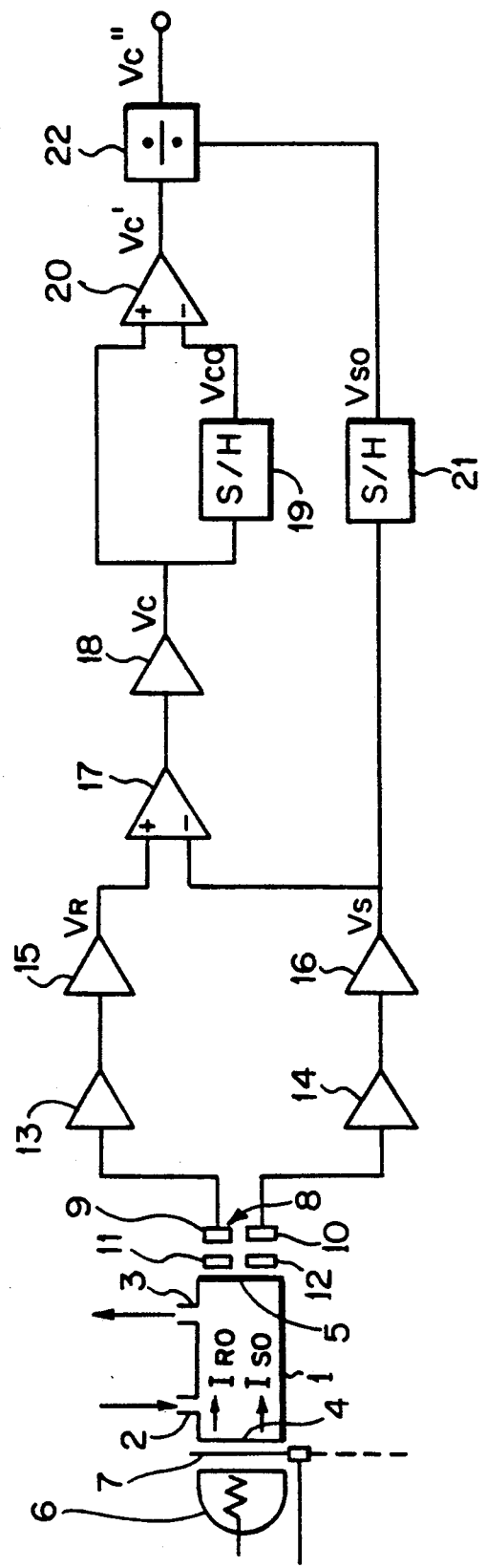
FIG. 1 is a schematic block diagram showing an electrical schematic of an infrared analyzer according to one preferred embodiment of the present invention.

Referring to FIG. 1, an electrical schematic of a first preferred embodiment of an infrared gas analyzer is disclosed. This embodiment is of a so-called one light source, one cell type of infrared analyzer. A light cell 1 is provided with an inlet port 2 that can be appropriately connected to a source of a sample gas. An outlet port 3 can exhaust the sample gas. The sample cell 1 includes a pair of cell windows 4 and 5 that are permeable to the infrared rays that can be generated from an infrared ray source 6 having a constant intensity bandwidth of radiation that extends beyond the absorption characteristic of the gas to be sampled. For example, in the case where the sample gases to be measured are HC, CO, and $CO_2$, the measuring wavelength band of HC is set at 3.4 $\mu$m, that of CO is set at 4.6 $\mu$m, and that of $CO_2$ is set at 4.3 $\mu$m. The reference gas is set at 3.8 $\mu$m. The light source 6 can provide a wavelength band sufficient to cover this spectrum of 3.4 $\mu$m to 4.6 $\mu$m such as a heat generating resistor of nichrome wires. As can be appreciated, the operator will generally be aware of the particular gases that should be contained in the sample, e.g., the exhaust gases from an engine.

The infrared ray source 6 is offset from the cell window 4 to accommodate a light chopping modulator 7 that can be driven by a mechanism (not shown). A timing of the frequency of the chopper 7 with the subsequent signal processing (which is known in the art) has been omitted to simplify the explanation.

A sensor 8 comprises a pair of detectors 9 and 10 for measuring, respectively, a comparative wavelength through detector 9 and a measuring wavelength through detector 10. The respective detectors are arranged in parallel and receive light that has passed through the cell window 5 of the sample cell 1. A pair of respective band-pass filters 11 and 12 are positioned between the cell window 5 and each of the respective detectors 9 and 10. The band-pass filter 12 is permeable to infrared rays having a characteristic absorption wavelength that can be absorbed by a specific ingredient gas that is desired to be measured in the sample gas. Comparative wavelength detector 9 is also provided with a band-pass filter 11, which is capable of transmitting infrared rays having a wavelength that is not absorbed, or at least a negligible amount of absorption occurs, by this specific ingredient gas. Detectors 9 and 10 output a signal proportional to the energy of the infrared rays impinging thereon, and respective preamplifiers 13 and 14 can amplify and rectify this output. Amplifier 13 is connected to the input of a comparative signal amplifier 15 to provide an appointed gain to the comparator wavelength signal as a comparator signal $V_R$. Likewise, measured signal amplifier 16 has its input connected to the output of the preamplifier 14 for amplifying a measured signal at an appointed gain to provide a measured signal $V_S$. The gains are predetermined to provide a balanced signal magnitude or normalization for subsequent processing.

A subtracter circuit 17 has its positive input terminal connected to the comparator signal amplifier 15 and its negative terminal input to the measured signal amplifier 16. The difference between the comparator signal $V_R$ and the measured signal $V_S$ is again amplified by an amplifier 18 to provide a differential signal $V_C$.

Thus, in the measurement of the amount of concentration of a specific gas element in a sample gas, the sample gas is introduced into cell 1 and is subject to the infrared rays from the light source 6. These rays are intermittently applied by the modulation of the chopper 7. The infrared rays selected include a characteristic absorption wavelength that can be absorbed by a specific ingredient gas that is desired to be measured in the sample gas. Detector 10 measures the amount of absorption through the band-pass filter 12 to finally provide an amplified measured signal $V_S$. For purposes of comparison, the detector 9 also measures the infrared rays passing through the band-pass filter 11, to ultimately provide an amplified comparator signal $V_R$. The signal $V_S$ is subtracted from the signal $V_R$ in the subtracter circuit 17, and an output of this differential signal is then amplified to the amplifier 18 to provide a differential signal $V_C$ or a concentration signal. A sample hold circuit or signal memory 19 is capable of storing and holding an input signal such as the value of measurement from the amplifier 18 when there is no gas, that is, a zero gas state is established in the sample cell, for a calibration procedure. This measurement value can be held in the sample hold circuit 19 and its output can be applied to a negative terminal of a subtracter circuit 20, which can also receive, on its positive terminal, a concentration signal $V_C$ from a measurement of a sample gas. The difference between a zero gas comparative signal $V_{RO}$, and a measured signal (zero gas measured signal) $V_{SO}$ during the measurement of the zero gas can be memorized in the signal memory 19 with a gain $G_C$ of the amplifier 18, to form the signal $V_{CO}$. In a measurement of a sample gas, the concentration signal $V_C$ can have the $V_{CO}$ signal subtracted in subtracter circuit 20 to provide a subtraction output $V_C'$ in a form that is thereby corrected for any drift from a zero point.

A sample hold circuit 21 or signal memory can also memorize the zero gas measurement signal $V_{SO}$ to provide for span calibration. Reference numeral 22 designates a divider circuit for dividing the subtracted output $V_C'$ by the zero gas measured signal $V_{SO}$. The resulting output $V_C''$ is a signal proportional to merely the absorption of infrared rays by the specified ingredient gas.

Since the zero gas measured signal $V_{SO}$ is the measurement signal that is derived during a measurement operation without any gas in the sample cell 1, its signal is dependent upon the characteristics of the light quantity of the light source 6, the characteristics of the cell windows 4 and 5, e.g., stain or discoloration, the detection sensitivity of the detectors 9 and 10, and any change or variation in the amplifying factors of the amplifiers 16, etc.

On the other hand, the subtraction output $V_C'$, which is output after the correction of the zero drift, is influenced by the light quantity of the light source 6, the characteristics of the cell windows 4 and 5, the detection sensitivity of the detectors 9 and 10, the same change in any amplifying factor of the amplifier 16, etc., and further includes the characteristic of the absorption of infrared rays by the specified ingredient gas. As a result, the output $V_C''$ obtained by dividing the subtraction output $V_C'$ by the zero gas measured signal $V_{SO}$ in the divider circuit 22 produces a signal proportional to merely the absorption of infrared rays by the specified ingredient gas. In essence, the extraneous influence of the other factors of the measurement system have been compensated for and removed from the output signal. As a result, an accurate output signal, which has been corrected in both zero drift and span drift, can be obtained.

The zero calibration and span calibration can be conducted simultaneously, as can be determined from the following mathematical expressions.

Again referring to FIG. 1, the energy of an infrared ray having a comparative wavelength radiating from the light source 6 is $I_{RO}$. The energy of the infrared rays having a measured wavelength radiating from the light source 6 is $I_{SO}$. The transmissivity of the cell 1 can be defined by a factor $T_C$, and the absorption of infrared rays by the specified ingredient gas in the sample gas (hereinafter "infrared absorption") being represented by x where $0 \leq x \leq 1$. In this regard, without any gas or a zero gas condition, $x=0$.

The energy $I_S$ of the infrared rays reaching the comparator wavelength detector 9 and the energy of the infrared rays $I_R$ of the infrared rays reaching the measuring wavelength detector 10 are represented by the following expressions, respectively:

$$I_R = I_{RO} T_C \tag{1}$$

$$I_S = I_{SO} (1-x) T_c \tag{2}$$

Assuming that the sensitivity of the comparative wavelength detector 9 is $\alpha_R$, the total gain from the preamplifier 13 to the amplifier 15 being $G_R$, the sensitivity of the measuring wavelength detector 10 being $\alpha_S$, and the total gain from the preamplifier 14 to the amplifier 16 being $G_S$, the comparative signal $V_R$ and the measured signal $V_S$ is expression by the following equations, respectively:

$$\begin{aligned} V_R &= I_R \cdot \alpha_R \cdot G_R \\ &= I_{RO} \cdot T_C \cdot \alpha_R \cdot G_R \end{aligned} \tag{3}$$

$$\begin{aligned} V_S &= I_S \cdot \alpha_S \cdot G_S \\ &= I_{SO} \cdot (1-x) \cdot T_C \cdot \alpha_S \cdot G_S \end{aligned} \tag{4}$$

If the gain of the amplifier 18 is $G_C$, the concentration signal $V_C$, which is the output of the amplifier 18, is expressed by the following:

$$\begin{aligned} V_C &= G_C \cdot (V_R - V_S) \\ &= G_C \cdot T_C \cdot \{I_{RO} \cdot \alpha_R \cdot G_R - \\ &\quad I_{SO} \cdot (1-x) \cdot \alpha_S \cdot G_S\} \end{aligned} \tag{5}$$

If the zero gas comparative signal is $V_{RO}$ and the zero gas measured signal is $V_S$ with a zero gas ($x=0$), then this condition will exhibit no absorption at the characteristic absorption wavelength of the specified ingredient gas, and the following equations will be valid:

$$\begin{aligned} V_{RO} &= I_{RO} \cdot T_C \cdot \alpha_R \cdot G_R \\ &= V_R \end{aligned} \tag{6}$$

$$V_{SO} = I_{SO} \cdot T_C \cdot \alpha_S \cdot G_S \tag{7}$$

The resulting differential signal $V_{CO}$, which is the output of the amplifier 18 at this time, will be expressed by the following equation:

$$V_{CO} = G_C \cdot (V_{RO} - V_{SO}) \tag{8}$$

As mentioned above, this differential signal $V_{CO}$ can be memorized by the sample hold circuit 19 and applied to the subtracter circuit 20.

$V_C$ will equal $V_{CO}$ during the measurement of a zero gas situation, and therefore $V_C'$ will equal zero. In general, this subtraction output $V_C'$ which is output from the subtracter 20 can be expressed in the following manner:

$$V_C' = V_C - V_{CO} \tag{9}$$

The subtraction output $V_C'$ during the measurement of a sample gas is expressed by the following equation, which is derived from Equations (5), (6), (7), (8), and (9):

$$V_C' = G_C \cdot T_C \cdot I_{SO} \cdot \alpha_S \cdot x \cdot G_S \tag{10}$$

As can be seen from Equation (10), the subtraction output $V_C'$ is proportional to the absorption of infrared rays x, the light quantity of the light source $I_{SO}$, the transmissivity $T_C$ due to any discoloration of the cell windows 4 and 5, the amplifier gain, etc. However, since the signal memory 21 memorizes the zero gas measurement signal $V_{SO}$ during the measurement of the zero gas state, and this value is provided to the divider circuit 22, division output $V_C''$ of the divider circuit 22 can be expressed by the following:

$$V_C'' = V_C'/V_{SO} \tag{11}$$

As a result, combining Equation (11) and Equations (7) and (10) can provide the following output:

$$\begin{aligned} V_C'' &= (G_C \cdot T_C \cdot I_{SO} \cdot \alpha_S \cdot x \cdot G_S)/ \\ &\quad (I_{SO} \cdot T_C \cdot \alpha_S \cdot G_C) \\ &= G_C \cdot X \end{aligned} \tag{12}$$

As can be seen from Equation (12), the output signal is proportional to the absorption x of the infrared rays. In summary, the output signal has all other factors removed from it that can influence the signal that are not specifically related to the desired specimen gas that is to be measured.

In those circumstances where the span gas has a known concentration, the relationship between the absorption x of the infrared rays and the concentration of the specified ingredient gas can also be easily obtained from the output $V_C'$. Thus, it would be sufficient for the gain $G_C$ of the amplifier 18 to be regulated so that the appointed output may be obtained. As can be readily appreciated, the signal treatment can also be performed with the assistance of a computer, with the signals being digitized and then accordingly mathematically processed by the above equations.

Figure 2:
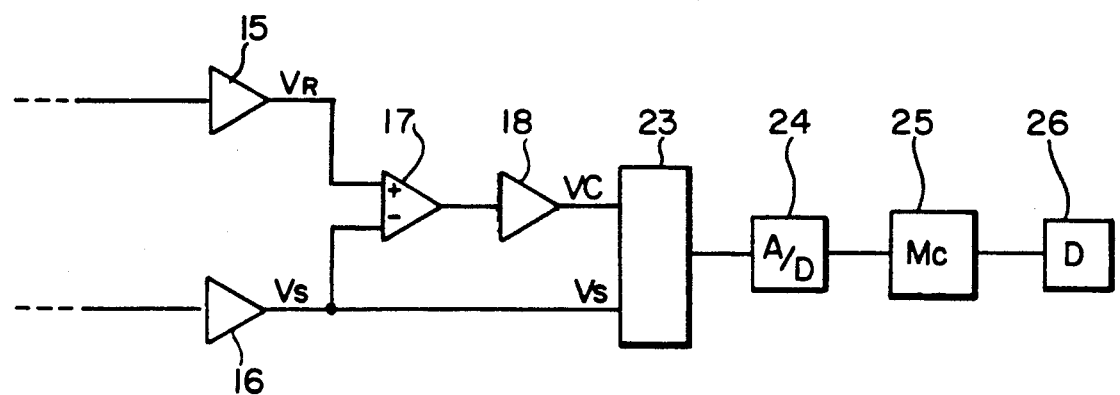
FIG. 2 is a block diagram showing the principal parts of an infrared analyzer according to another preferred embodiment of the present invention.

Another embodiment of the present invention is disclosed in FIG. 2, and discloses a signal processing with the assistance of a microcomputer. The same reference numbers as set forth in FIG. 1 are used for common parts.

A measured signal $V_S$, which is an output of the measured signal amplifier 16, and a concentration signal $V_C$, are obtained by amplifying the difference between a comparative signal $V_R$, which is an output of a comparative signal amplifier 15, and the measured signal $V_S$ in an amplifier 18. The output is subject to conversion from an analog into a digital signal and an A-D converter 24. An input changeover device 23 is connected to the A-D converter 24. The respective converted signals of the $V_C$ and $V_S$ measurements are then processed by a microcomputer 25. In this regard, the microcomputer 25 can also memorize the zero gas measured signal $V_S$ during the measurement of a zero gas state, and also a signal $V_{CO}$ by means of an internal memory, to thereby enable the execution of a process to perform Equations (9) and (11) through program steps, as known in the computer program field. As a result, the same signal processing can be accomplished for the infrared analyzer as performed by the circuitry shown in FIG. 1. In FIG. 2, the reference number 26 designates a display for displaying the calculated output result.

In the embodiments of FIGS. 1 and 2, a single light source cell infrared analyzer has been disclosed. As can be appreciated, however, the present invention is not limited to only a single infrared analyzer. Thus, the present invention can be applied not only to an infrared analyzer wherein a reference cell is disposed in parallel to a sample cell, but also to a multicomponent infrared analyzer for analyzing a plurality of components at the same time. Thus, the present invention can be applied to each form of infrared analyzer wherein a comparative signal $V_R$ and a measured signal $V_S$ are separately taken, and the difference between signals can be output as a concentration signal $V_C$.

Figure 3:
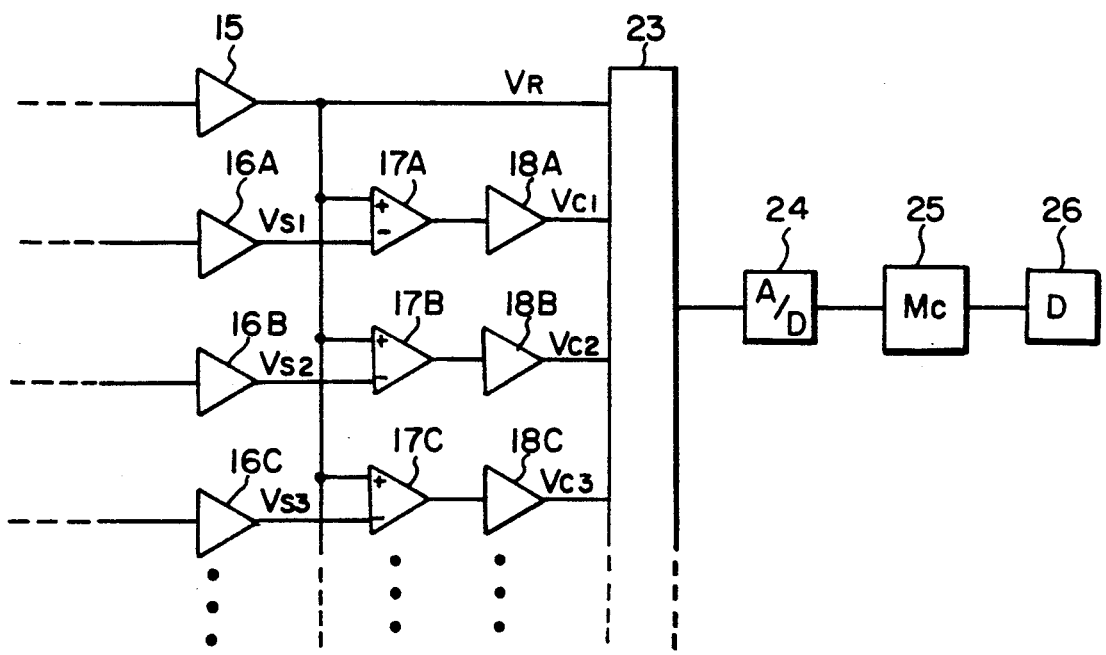
FIG. 3 is a schematic block diagram showing the principal parts of an infrared analyzer according to a third preferred embodiment of the present invention.

FIG. 3 discloses another preferred embodiment of the present invention as applied to a multicomponent analyzer. In FIG. 3, the reference numerals 16A, 16B, 16C designate respective signal amplifiers for amplifying outputs of a plurality of measured wavelength detectors (not shown). Each of these detectors can respond respectively to one of a plurality of gas ingredients in a measured sample to output corresponding measured signals $V_{S1}$, $V_{S2}$, $V_{S3}$. Reference numerals 17A, 17B, 17C designate subtracter circuits that are provided to correspond to the gas ingredients to be measured. An input terminal to each of the subtracters is also connected to the output of the amplifier 15. The outputs from the subtracter circuits 17A, 17B, 17C are applied to the amplifiers 18A, 18B, 18C for amplifying the differential signals between the comparative signal $V_R$ and the outputs of each of the measured signal amplifiers to provide amplifier output concentration signals $V_{C1}$, $V_{C2}$, $V_{C3}$, respectively. An input changeover device such as, for example, multiplexer circuit 23, can apply, respectively, these concentration signals $V_{C1}$, $V_{C2}$, $V_{C3}$, and $V_{CR}$ to an analog-to-digital converter 24.

Measured signals $V_{S10}$, $V_{S20}$, $V_{S30}$ corresponding to the respective gas ingredients in the measured samples can be determined by Equation (8) on the basis of the comparator signal $V_R$ during the measurement of the zero gas state and the outputs $V_{C10}$, $V_{C20}$, $V_{C30}$ which were obtained by amplifying the differences in the measurement of the zero gas. This can be represented by the following equations:

$$V_{S10} = V_{RO} - V_{C10}/G_C \quad (13)$$

$$V_{S20} = V_{RO} - V_{C20}/G_C \quad (14)$$

$$V_{S30} = V_{RO} - V_{C30}/G_C \quad (15)$$

As can be realized, the same effect as in the above-described embodiments can be achieved through the use of microcomputer processing, wherein the signals $V_{S10}$, $V_{S20}$, $V_{S30}$, and $V_{C10}$, $V_{C20}$, $V_{C30}$ are memorized and held within the microcomputer 25, and are used for carrying out the calculations in accordance with Equations (9) and (10) for each of the various gas elements that are sought to be measured.

As can be appreciated, in accordance with the present invention, a measurement signal that is made when there is no gas or a zero gas state in the sample cell can be memorized, and additional calculations can be carried out on the basis of this memorized signal so that it is not required to introduce an expensive span gas into the cell when the span calibration is conducted. Thus, not only can the span calibration be simply and inexpensively conducted, but also the zero calibration and the span calibration can be accomplished at the same time in a relatively economical short time period.

While the above embodiment has been disclosed for the best modes contemplated by the inventors, it should be realized that these examples should not be interpreted as limiting, because artisans skilled in the electronic measurement field, once given the present teaching, can vary from these specific embodiments. Accordingly, the scope of the present invention should be determined solely from the following claims.

What is claimed is:

1. An infrared analyzer comprising:
   a sample cell for holding a specimen gas to be analyzed to determine the amount of a predetermined gas, if any;
   a source of infrared rays, for passing through the sample cell;
   means for measuring the infrared rays that have passed through the sample cell to provide one measurement signal indicative of absorption of infrared rays, and another comparative signal indicative of the intensity of infrared rays through the sample cell;
   a subtracter circuit for providing an output difference signal between the measured signal and the comparator signal;
   means connected to the output of said subtracter circuit for storing an output difference signal when a zero gas condition relative to the specimen gas is established in the sample cell;
   means connected to the measurement means for holding the zero gas measurement signal, and
   means for processing the output difference signal with a sample gas in the cell by modifying the output difference signal with the zero gas difference signal and the zero gas measurement signal to provide an output signal representative of the concentration of the predetermined gas.

2. The infrared analyzer of claim 1 further including amplifier means for amplifying the measurement signals to normalize the same for subsequent processing.

3. The infrared analyzer of claim 1 where the means for measuring includes a band-pass filter and a detector for both the measurement signal and the comparative signal infrared rays.

4. The infrared analyzer of claim 1 where the means for storing includes a sample hold circuit.

5. An infrared analyzer comprising:
a sample cell for holding a specimen gas to be analyzed to determine the amount of a predetermined gas, if any;
a source of infrared rays, for passing through the sample cell;
means for measuring the infrared rays that have passed through the sample cell to provide one measurement signal indicative of absorption of infrared rays, and another comparative signal indicative of the intensity of infrared rays through the sample cell;
a subtracter circuit for providing an output difference signal between the measured signal and the comparator signal;
means connected to the output of said subtracter circuit for storing an output difference signal when a zero gas condition relative to the specimen gas is established in the sample cell;
means connected to the measurement means for holding the zero gas measurement signal, and
means for processing the output difference signal with a sample gas in the cell by subtracting the output difference signal with the zero gas difference signal and dividing the result with the zero gas measurement signal to provide an output signal representative of the concentration of the predetermined gas.

6. An infrared analyzer comprising:
a sample cell for holding a specimen gas to be analyzed to determine the amount of a predetermined gaseous component, if any;
a source of infrared rays, for passing through the sample cell;
means for measuring the infrared rays that have passed through the sample cell to provide one measurement signal indicative of absorption of infrared rays, and another comparative signal indicative of the intensity of infrared rays through the sample cell;
means for digitizing the respective measurement and comparative signals;
computing means for processing the measurement and comparative signals including subtracting means for providing an output difference signal between the measured signal and the comparative signal, means connected to the output of said subtracting means for storing an output difference signal when a zero gas condition relative to the specimen gas is established in the sample cell, means connected to the measurement means for holding the zero gas measurement signal, and
means for processing the output difference signal with a sample gas in the cell by modifying the output difference signal with the zero gas difference signal and the zero gas measurement signal to provide an output signal representative of the concentration of the predetermined gas.

7. The infrared analyzer of claim 6 further including a plurality of sample cells for receiving infrared rays and a plurality of measuring means, to provide a respective measurement signal and comparative signal for each sample cell and means for applying the resulting digitized signals to the computing means wherein an output signal indicative of a gaseous component in each cell is produced.

* * * * *